US005719031A

United States Patent [19]

Haugland et al.

[11] Patent Number: 5,719,031
[45] Date of Patent: Feb. 17, 1998

[54] DYE LABELED POLYMERS AS REAGENTS FOR MEASURING POLYMER DEGRADATION

[75] Inventors: Richard P. Haugland; Mingjie Zhou, both of Eugene, Oreg.

[73] Assignee: Molecular Probes, Inc., Eugene, Oreg.

[21] Appl. No.: 696,544

[22] Filed: Aug. 14, 1996

[51] Int. Cl.$^6$ .......... G01N 33/573; G01N 33/68; C07K 17/00

[52] U.S. Cl. .............. 435/7.4; 435/6; 435/7.5; 435/14; 435/24; 436/529; 436/530; 530/391.3; 530/360; 530/362; 530/402; 530/810; 530/813; 530/814; 536/123.1

[58] Field of Search .............. 435/7.4, 6, 7.5, 435/14, 24; 436/529, 530; 530/391.3, 360, 362, 402, 810, 813, 814; 536/123.1

[56] References Cited

U.S. PATENT DOCUMENTS

| | | | |
|---|---|---|---|
| 4,774,339 | 9/1988 | Haugland et al. | 548/405 |
| 5,274,113 | 12/1993 | Kang et al. | 548/405 |
| 5,433,896 | 7/1995 | Kang et al. | 548/405 |
| 5,550,025 | 8/1996 | Walker | 435/6 |
| 5,567,596 | 10/1996 | Diamond et al. | 436/536 |
| 5,573,909 | 11/1996 | Singer et al. | 435/6 |

OTHER PUBLICATIONS

Farmer, et al., Anal. Biochem. 197, 347 (1991).
Bolger, et al., Biotechniques 17, 585 (1994).
Haugland, Handbook of Fluorescent Probes and Research Chemicals, 5th Ed., Molecular Probes, Inc., Eugene, OR (1992–1994).
Davidson, The Biochemistry of the Nucleic Acids (1976), Chapman and Hall, Science Paperbacks, Great Britain (1972), Table of Contents only.
Wittung, et al., Nature 368, 561 (1994).
Wiesner et al., Anal. Biochem. 121, 290 (1982).
Ashcom et al. Anal. Biochem. 176, 261 (1989).
Schade et al., Amer. Ass. Dental Res. 73rd annual meeting, Poster #337, Mar. 9, 1995.
Haugland et al., Joint Meeting of the Amer. Soc. for Biochem. and Molec. Biol., the Amer. Soce. for Investigative Pathology and Amer. Assoc. of Immunologists, New Orleans, Louisiana, USA, Jun. 2–6, 1996. FASEB Journal 10 (6), 1996 A 1405. ISSN: 0892–66.

*Primary Examiner*—Mary E. Ceperley
*Attorney, Agent, or Firm*—Allegra J. Helfenstein; Anton E. Skaugset

[57] ABSTRACT

This invention relates to polymers labeled with fluorescent dye to the point that significant fluorescence quenching occurs, such that degradation of the polymer results in fluorescence enhancement. The resulting fluorescence enhancement is useful for measuring the degradation of such polymers, for example as a result of enzymatic hydrolyis of a protein, carbohydrate, nucleic acid, or other natural or synthetic polymer.

40 Claims, 7 Drawing Sheets

DYE LABELED POLYMERS AS REAGENTS FOR MEASURING POLYMER DEGRADATION

FIELD OF THE INVENTION

This invention relates to polymers labeled with a borapolyaza-s-indacene fluorescent dye to the point that significant fluorescence quenching occurs, such that degradation of the polymer results in fluorescence enhancement. The resulting fluorescence enhancement is useful for measuring the degradation of such polymers, for example as the result of enzymatic hydrolyis of a protein, polysaccharide, nucleic acid, or other natural or synthetic polymer.

BACKGROUND

This invention relates to polymers that are multiply labeled with a borapolyaza-s-indacene fluorescent dye for measuring the degradation of such polymers. Sufficient dye is covalently bound to a polymer such that the fluorescence of the attached fluorophores is substantially quenched. When the dye-labeled polymer is exposed to conditions that cause degradation of the polymer, such as action of an enzyme that selectively or non-selectively cleaves the polymer to smaller fragments, the resulting increase in the fluorescence intensity correlates to the degree of degradation (see FIG. 1). The invention is useful for many purposes, including detecting the presence or absence of enzymatic activity in a solution, a cell, a cell extract, or on or in a matrix. Detection of enzymatic activity in biological growth or purification media is important for avoiding breakdown of biological materials by contaminated solutions, for calibrating biological and diagnostic assays, for detecting enzymatic activity in normal and diseased cells and tissues, and for detecting the presence of desirable or undesirable organisms. Enzyme activity measurements are useful for visualizing metabolism in living cells, as diagnostic tools, as detection reagents for various assays, and for numerous other purposes. The invention is also useful for monitoring other conditions that cause degradation of polymers, such as photolysis or treatment with chemical agents such as acid, base or oxidizing agents.

It is well known that fluorescence of dyes can be quenched on conjugation to polymers when a large number of dyes are conjugated to the polymer. Because of this quenching, most biopolymers, such as fluorescent antibodies that are to be used as detection reagents, are prepared with a relatively low degree of substitution: Typically less than 8–10 dyes per 150,000 daltons for an IgG. By increasing the degree of substitution, however, materials have been developed that are useful as novel substrates for enzymatic or other degradation conditions.

Other uses of fluorescent labeled polymers as enzyme substrates are known. One method uses the incorporation of energy transfer pairs of dye molecules that are covalently immobilized to the same polymer in close proximity to each other. This familiar principle of excited state energy transfer quenching has been used previously to prepare low molecular weight energy transfer-quenched fluorogenic substrates having well defined sequences for specific peptidases of less than about 15 amino acid residues, as well as for continuous proteolytic activity (e.g. Farmer, et al., ANAL. BIOCHEM. 197, 347 (1991). By contrast, the substrates of this invention contain many more molecules of fluorescent borapolyaza-s-indacene dyes of the same chemical structure per polymer, which results in a higher fluorescence yield of the overall hydrolysis product.

Assay conditions and materials using fluorescence quenched polymeric substrates differ from similar enzyme assays that use other fluorescent dye-labeled polymers and fluorescence polarization for detection. In the polarization-detected assays, energy transfer between fluorophores results in depolarization and a significant loss in sensitivity. Consequently, the fluorescent dye-labeled polymers that are suitable for polarization assays will have minimal quenching, which necessitates labeling of the polymer with an average of less than one dye per biopolymer. Therefore, the labeled polymers used for a fluorescence quenching-based assay will not work well for a fluorescence polarization-based assay and vice versa.

Some current methods for detecting protease activity require extensive manipulation and separation steps that increase the chance of error. For example, in the fluorescein thiocarbamoyl CFTC) casein protease assay described by Bolger, et al. in BIOTECHNIQUES 17, 585 (1994), unhydrolyzed protein must be precipitated with trichloroacetic acid, separated by centrifugation, transferred for measurement and then pH-adjusted for fluorescein signal enhancement (see FIG. 4). The assay of the invention, however, allows direct sample measurement using a standard fluorometer or fluorescence microplate reader and fluorescein excitation and emission wavelengths. The determination of protease activity is up to 100 times more sensitive than the fluorescence-based FTC-casein assay when the borapolyaza-s-indacene-labeled casein substrate is used according to the invention.

SUMMARY OF THE INVENTION AND DESCRIPTION OF PREFERRED EMBODIMENTS

The Labeled Polymer

Figure 1:
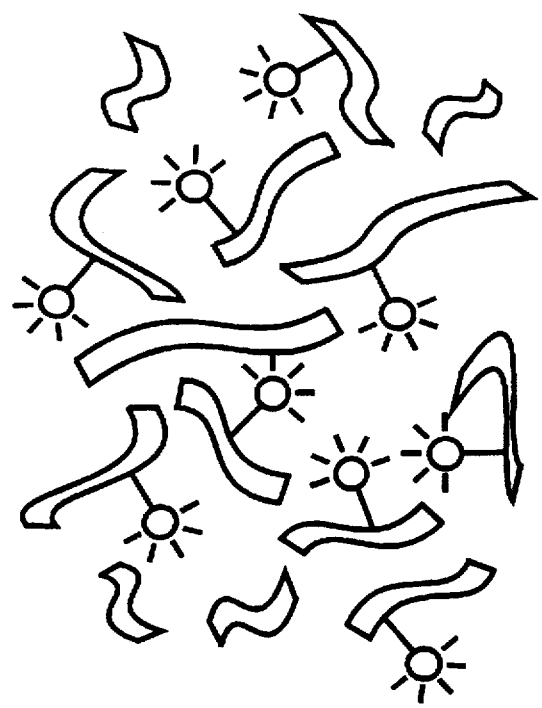
FIG. 1: A graphic depiction of a highly quenched fluorescent polymer being cleaved to smaller fragments, resulting in an increase in fluorescence.
Figure 1:
Figure 1:
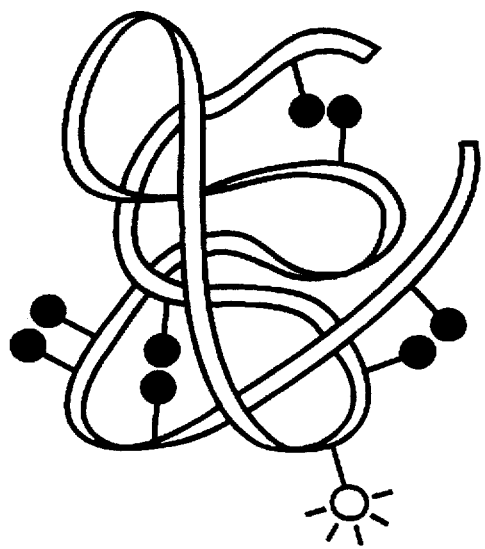

The labeled polymer used to practice this invention comprises a polymer that is covalently labeled with at least two molecules of a single borapolyaza-s-indacene fluorescent dye, such that the fluorescence of the dyes attached to the polymer is substantially quenched.

Fluorescent Dyes

Several variations of reactive borapolyaza-s-indacene dyes that are suitable for covalent attachment to polymers are described in U.S. Pat. Nos. 4,774,339 (Haugland, et al., 1988); 5,274,113 (Kang, et al., 1993); and 5,433,896 (Kang, et al., 1995), each of which patents are incorporated by reference. A number of these borapolyaza-s-indacene dyes are commercially available, including those described by Hangland, HANDBOOK OF FLUORESCENT PROBES AND RESEARCH CHEMICALS (5th Ed. Molecular Probes, Inc., Eugene OR 1992–1994), which is incorporated by reference.

All fluorescent dyes bound to the labeled polymer have the same chemical structure. The fluorescent dye used to label the polymer has a molecular weight less than 1500 daltons in its unconjugated form. The dye is selected so as to have its longest wavelength absorption peak beyond the predominant absorption of the polymer (e.g. beyond about 300 nm for most proteins, beyond about 280 nm for most polynucleotides and beyond about 240 nm for most pure polysaccharides) so as to be excitable separately from the polymer. The preferred dyes are those that absorb maximally beyond 450 ram; that have extinction coefficients greater than 30,000 $cm^{-1}M^{-1}$, more preferably greater than about 50,000 $cm^{-1}M^{-1}$; and that have quantum yields in their unconjugated forms greater than about 0.2, preferably greater than about 0.4, more preferably greater than 0.6.

In one embodiment of the invention the polyazaindacene dyes have the following formula (I), where one of the substituents on the polyazaindacene dye, as defined below, is modified for covalent attachment to the polymer by a reactive group:

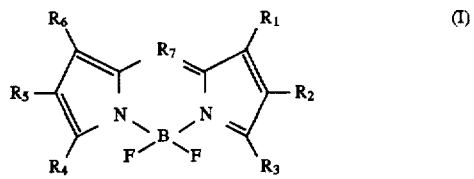
(I)

wherein $R_1$–$R_6$, which may be the same or different, are hydrogen, halogen, nitre, sulfo, cyano, alkyl, perfluoroalkyl, alkoxy, alkenyl, alkynyl, cycloalkyl, arylalkyl, acyl (wherein the alkyl portions of each contain fewer than 20 carbons, typically fewer than 10 carbons); or substituted or unsubstituted aryl or heteroaryl. Typically, no more than 4 of $R_1$–$R_6$, which may be the same or different, are non-hydrogen.

$R_7$ is nitrogen; or methine; or halogen-, cyano-, alkyl-, perfluoroalkyl-, alkoxy-, alkenyl-, alkynyl-, cycloalkyl-, arylalkyl-, acyl-, (wherein the alkyl portions of each contain fewer than 20 carbons, typically fewer than 10 carbons) aryl- or heteroaryl-substituted mSethine. Typically $R_7$ is methine.

Alternatively, R7 is methine; or alkyl-, perfluoroalkyl-, cycloalkyl-substituted mSethine (wherein the alkyl portions of each contain fewer than 20 carbons); or aryl- or heteroaryl-substituted methine; and adjacent substituents $R_1$–$R_2$, and $R_5$–$R_6$, each combine to form a fused benzo ring according to the formula (II):

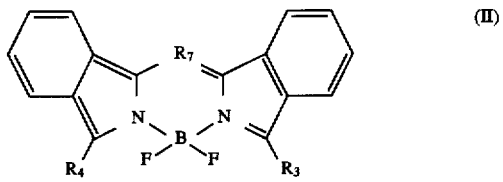
(II)

where each fused benzo ring optionally contains substituents, which may be the same or different, that are hydrogen, halogen, nitre, sulfo, cyano, alkyl, perfluoroalkyl, alkoxy, alkenyl, alkynyl, cycloalkyl, alkylthio, alkylamido, amine, monoalkylamino, dialkylamino (wherein the alkyl portions of each contain fewer than 20 carbons, typically fewer than 10 carbons); or substituted or unsubstituted aryl, heteroaryl; aryl-amido, heteroaryl-amido, aryl-oxy, heteroaryl-oxy, aryl-amino, or heteroaryl-amino; or 1–2 additional fused benzo or heteroaromatic rings that are optionally unsubstituted or substituted.

The reactive group is introduced during the synthesis of the dye, or by chemical modification of the dye according to methods generally known in the art (e.g. Haugland, HANDBOOK, supra). Some examples of this type of reactivity include:

1. The activation of amine groups to yield reactive species, including isocyanates, isothiocyanates, 4,6-dichloro-1,3,5-triazines, maleimides or haloacetamides;

2. The conversion of carboxylic acid groups to activated derivatives, including symmetric and mixed anhydrides, acid halides, acyl azides, acyl hydrazides and various activated esters, including succinimidyl esters, p-nitrophenyl esters and pentafluorophenyl esters;

3. The conversion of sulfonic acid groups to sulfonyl chlorides and sulfonyl fluorides;

4. The conversion of alcohols groups to ethers, esters, urethanes, carbonates or alkylating agents that include sulfonate esters and halides;

5. The conversion of thiols to thioethers, thioesters and disulfides.

Polymers

The polymer used for the invention is selected to contain at least one chemical bond that is cleaved by the condition being investigated. For example, where the degradation condition is a hydrolytic enzyme, the polymer is selected to contain at least one enzyme-clearable bond. Typically the polymer is selected to contain several bonds that are cleaved by the subject enzyme, where cleavage results in changes in structure of the polymer or results in fragments of lower molecular weight.

Suitable polymers include but are not limited to natural and synthetic polypeptides and proteins, polysaccharides (including agarose, cellulose, dextrans, FICOLL polysucrose, heparin, glycogen, amylopectin, mannan, inulin, and starch), polymers of nucleic acids (including ribonucleic acids, deoxyribonucleic acids, and peptide nucleic acids). Synthetic or partially synthetic polymers such as polyesters and polyamides are suitable provided that they contain at least one polymeric bond that is cleaved by the conditions under study.

Typically the polymers are naturally or synthetically polymerized from subunits that have a biological function (e.g. sugars, amino acids, and nucleic acids, and combinations thereof) and are called biopolymers. Typically such biopolymers have molecular weights greater than about 4000 daltons, more typically greater than about 10,000 daltons. Protein polymers typically have molecular weights between 10,000 daltons and 200,000 daltons but certain proteins such as collagen or its more soluble derivative gelatin may have much higher molecular weights. The most suitable protein polymers for general use are those that have molecular weights greater than about 25,000, that have several lysine residues and that have relatively low secondary structure. Nucleic acid polymers may have molecular weights of up to several million daltons. The preferred polymers are those that are completely or partially soluble in aqueous medium, although poorly soluble polymers or immobilized polymers that are enzymatically hydrolyzed to soluble fluorescent products are also suitable in some cases.

The nucleic acid polymer may be RNA or DNA, or a mixture or a hybrid thereof. Any DNA is optionally single-, double-, triple-, or quadruple-stranded DNA; any RNA is optionally single stranded ("ss") or double stranded ("ds"). The nucleic acid may be a natural polymer (biological in origin) or a synthetic polymer (modified or prepared artificially). The nucleic acid polymer (preferably containing at least 8 bases or base pairs, typically greater than 22 bases or base pairs) may be present as nucleic acid fragments, oligonucleotides, or larger nucleic acid polymers with secondary or tertiary structure. The nucleic acid polymer optionally contains one or more modified bases or links. For example, the modified base can be a naturally occurring modified base such as ψ (pseudouridine) in tRNA, 5-methylcytosine, 6-methylaminopurine, 6-dimethylaminopurine, 1-methylguanine, 2-methylamino-6-hydroxypurine, 2-dimethylamino-6-hydroxypurine, or other known minor bases (see, e.g. Davidson, THE BIO-CHEMISTRY OF THE NUCLEIC ACIDS (1976)) or is synthetically altered to contain an unusual linker such as morpholine-derivatized phosphates (AntiVirals, Inc., Corvallis, Oreg.), or peptide nucleic acids, which have bases attached through an uncharged peptide backbone, such as N-(2-aminoethyl)glycine units as described by Wittung, et at., Nature 368, 561 (1994).

Most preferred because of their relatively greater ease of preparation are peptide or protein polymers or polysaccharide polymers. Examples include proteins or polysaccharides isolated from cells of plant or animal origin or from biological fluids. Glycoproteins labeled with dyes in either the protein or saccharide portion or in both portions are also suitable.

In one aspect of the invention, the multi-dye-labeled polymeric substrate contains one or more bonds that are non-selectively cleaved by a variety of enzymes under study, or by other conditions such as acid or base. In this way, one dye-labeled polymer can be used to detect the activity of several different enzymes (Example 3). Examples of such polymers are typically labeled proteins that contain a variety of linkages in the primary chain, such as casein, collagen (or gelatin), fibronectin and albumins. In another aspect of the invention the multi-dye-labeled polymeric substrate contains one or more bonds that are cleaved only by a specific enzyme or class of enzymes. Specificity is more likely in polysaccharide polymers, such as polysaccharides that have only one type of linkage. Such polymers include labeled dextrans, whose uncommon α-1,6-poly(glucose) linkages are specifically cleaved by the enzyme dextranase; labeled cellulose, which is cleaved by cellulase; labeled hyaluronic acid, which is a substrate for hyaluronidase; labeled heparin, which is a substrate for heparinase; and labeled mucopolysaccharides, which are substrates for lysozyme. Additional examples of selective polymeric substrates are a multi-dye-labeled ribonucleic acid, which is a substrate for ribonuclease CRNase) or a multi-dye-labeled deoxyribonucleic acid, which is a substrate for deoxyribonuclease I (DNase I).

Labeling Polymers

The fluorogenic substrates of this invention are usually prepared by the covalent modification of reactive groups on the polymer with two or more molecules of the selected reactive borapolyaza-s-indacene dye. Intermolecular reaction of an appropriate nucleophile or functional group on the polymer with the reactive group on the fluorophore results in the labeled polymer. The functional group is intrinsically incorporated in the polymer or is introduced to the polymer by chemical modification according to methods generally known in the art. Chemical modifications of polymers to make them reactive to dyes include, for instance, conversion of polysaccharides to amino- or carboxymethyl-polysaccharides, and modification of cytosine residues of a polynucleotide with an aliphatic diamine and bisulfite.

Useable functional groups on the polymer include, but are not limited to, amines, thiols, alcohols (including phenols), aldehydes, ketones, phosphates, imidazoles, hydrazines, hydroxylamines, di- and trisubstituted amines, thioethers, halides, epoxides, sulfonate esters, and carboxylic acids. A wide variety of other functional groups react under conditions well understood by one skilled in the art. Examples of some routes to useful conjugations include, but are not limited to, the pairs of reactive groups and functional groups listed in Table 1.

TABLE 1

Examples of reactions that form useful covalent linkages

| REACTIVE GROUP (on fluorophore) | FUNCTIONAL GROUP (on polymer) | YIELDING: (covalent linkage) |
|---|---|---|
| alcohols/phenols | alkyl halides | ethers |
| alcohols/phenols | acids | esters |
| alcohols/phenols | isocyanates | urethanes |
| alcohols/phenols | silyl halides | silicates |
| haloacetamides | thiols | thioethers |
| maleimides | thiols | thioethers |
| alkyl halides | thiols | thioethers |
| alkyl sulfonates | thiols | thioethers |
| alkyl halides | alcohols/phenols | ethers |
| alkyl sulfonates | alcohols/phenols | ethers |
| isocyanates | alcohols/phenols | urethanes |
| thiols | sulfonate esters | thioethers |
| thiols | haloacetamides | thioethers |
| thiols | maleimides | thioethers |
| thiols | epoxides | thioethers |
| amines/anilines | sulfonyl halides | sulfonamides |
| amines/anilines | carboxylic acids | carboxamides |
| amines/anilines | anhydrides | carboxamides |
| amines/anilines | activated esters* | carboxamides |
| amines/anilines | isocyanates | ureas |
| amines/anilines | isothiocyanates | thioureas |
| amines/anilines | chlorotriazines | aminotriazines |
| alkyl halides | amines/anilines | alkyl amines |
| activated esters* | amines | carboxamides |
| carboxylic acids | amines/anilines | carboxamides |
| anhydrides | amines/anilines | carboxamides |
| acyl halides | amines/anilines | carboxamides |
| aryl azides | amines/anilines | carboxamides/ureas |
| isocyanates | amines/anilines | ureas |
| isothiocyanates | amines/anilines | thioureas |
| chlorotriazines | amines/anilines | aminotriazines |
| sulfonyl halides | amines/anilines | sulfonamides |
| sulfonate esters | amines/anilines | alkyl amines |
| acrylamides | alkylenes | polyalkylenes |

*activated esters, as understood in the art, generally have the formula —COΩ, where Ω is a good leaving group (e.g. oxysuccinimidyl (—OC$_4$H$_4$O$_2$),-1-oxybenzotriazolyl (C$_6$H$_4$N$_3$O—); or a phenoxy group or phenoxy substituted one or more times by electron withdrawing substituents such as nitro, fluoro, chloro, cyano, or trifluoromethyl, or combinations thereof, used to form activated phenyl esters; or a carboxylic acid activated by a carbodiimide to form an anhydride or mixed anhydride —OCOR$^8$ or —OCNR$^8$NHR$^9$, where R$^8$ and R$^9$, which may be the same or different, are C$_1$–C$_6$ alkyl, C$_1$–C$_6$ perfluoroalkyl, or C$_1$–C$_6$ alkoxy; or cyclohexyl, 3-dimethylaminopropyl, or N-morpholinoethyl).

Typically the functional group on the polymer is a nucleophile that is an amine, a thiol, an alcohol, a carboxylic acid or is an aldehyde or ketone; and the reactive dye contains a reactive group that will react with the nucleophile, aldehyde or ketone under mild conditions. Amines, thiols, and alcohols are preferred because they are both more reactive, and more commonly available for the modification of biopolymers. Preferably the reactive group on the dye is a chloromethyl, an amine, a succinimidyl ester or a carboxylic acid.

Where the reactive dye contains a carboxylic acid (—COOH) or a reactive derivative of a carboxylic acid (—COOR$_x$), the reactive group R$_x$ is one that activates the carbonyl group of —COOR$_x$ toward nucleophilic displacement. In particular, R$_x$ is any group that activates the carbonyl towards nucleophilic displacement without being incorporated into the final displacement product. Typically, R$_x$ is a good leaving group, selected so that the dye contains an activated ester of a carboxylic acid: R$_x$ is optionally a symmetric anhydride that links two fluorophores, or a simple mixed anhydride of a fluorophore and a $C_2$–$C_8$ chloroformate, a $C_2$–$C_8$ carboxylic acid or perfluorinated carboxylic acid, a $C_1$–$C_8$ sulfonic or fluorinated sulfonic acid. Alternatively, the reactive group on the dye is an acyl azide or a carboxylic acid activated by a carbodiimide, or an ester of a phenol or a naphthol that is further substituted by at least one strong electron withdrawing group. Selected electron withdrawing groups, present in any combination, include but are not limited to nitro, sulfo, carboxy, alkali or alkaline earth metal salt of sulfo or carboxy, cyano, fluoro or chloro, or trifluoromethyl. Particularly suitable substituted aryl esters include nitrophenyl, sulfophenyl, pentafluorophenyl and pentachlorophenyl esters.

The functional group on the polymer and the reactive group on the fluorophore are attached directly by a single covalent bond, or attached via any useful spacer or linker. The spacer or linker is typically a covalent linkage having 1–20 nonhydrogen atoms selected from the group consisting of C, N, O and S, such that the linkage contains any combination of bonds selected from the group consisting of ether, thioether, amine, ester, carboxamide, sulfonamide or hydrazide bonds; single, double, triple or aromatic carbon-carbon bonds; or aromatic or heteroaromatic bonds. Typically, attachment is via a single bond or a polymethylene having 1–6 carbons.

Dyes that are selected to conjugate with polymers having free amine groups are preferably those dyes having a reactive group that is a succinimidyl or sulfosuccinimidyl ester. Amine-reactive dyes are of particular relevance as they are commonly used to label proteins and polypeptides, which typically possess multiple free amine groups. Amine-reactive dyes are additionally used to label materials that have been substituted with free amine groups, such as amino-dextrans; or amine-containing nucleotides, oligonucleotides or nucleic acids; or other amine-containing polymers.

Dyes that are selected to conjugate with polymers having free thiol groups are preferably those dyes having a reactive group that is a haloacetamide (—NH—(C=O)—CH$_2$—X), halomethylbenzamide (—NH—(C=O)—C$_6$H$_4$—CH$_2$—X), halomethyl (—CH$_2$—X) group (where X is Cl, Br or I) or a maleimido or an epoxide group. More preferably, the reactive group is an iodoacetamide or a halomethyl group.

Preferred alcohol- and phenol-reactive dyes are those dyes for which the reactive group is an isocyanate, 3,5-dichloro-2,4,6-triazine, acyl nitrile or is a phosphoramidite. Preferred photoreactive dyes have a reactive group that is an azidoperfluorobenzamido group.

Additional reactive groups include acyl nitriles or acyl hydrazides; other alternatives include a sulfonic acid, a sulfonyl halide, a sulfonyl azide, a hydroxy, a thiol, a semicarbazide, a carboxydiazide, a hydrazine, or a hydroxylamine.

The covalent bond that attaches the dye to the polymer is selected to be generally resistant to spontaneous hydrolysis and also resistant to the degradation conditions being studied, e.g. to the action of the target enzyme(s); or, where required, to acid or base. Typically the covalent bond between the dye and the polymer is a carboxamide, sulfonamide, ether or thioether but any bond between the dye that is chemically stable and resistant to the degradation conditions is suitable. Examples of reactions that are useful for preparing suitable substrates, among others, are the reaction of amines of casein or serum albumin with succinimidyl esters to form carboxamide bonds, reaction of the hydroxy group of hydroxyproline or of polysaccharide polymers with dichlorotriazines to form a chlorotriazinyl ether, or reaction of carboxylic acids of hyaluronic acid with an amine plus a coupling agent such as a carbodiimide to form a carboxamide. Alternatively, especially for modification of polynucleotides, chemical bonding can be accomplished by incorporation of a suitably-modified fluorescent nucleotide in a polymerization mixture at a ratio of labeled nucleotide to unlabeled nucleotide suitable to yield a suitable substrate (as defined below). Chemical bonding of the dye to the polymer can also be obtained by photolysis of an appropriate photoactivatable fluorescent dye in the presence of the polymer, by incorporation of dye-labeled amino acids into a peptide during a synthesis, by incorporation of the dye into a polymer using an enzyme such as terminal transferase for oligonucleotides or transglutaminase for some proteins or by introduction of abasic sites into oligonucleotides and modification with a hydrazide- or hydroxylamine-containing dye. Certain synthetic polymers can be labeled by incorporation of a sufficient fraction of a labeled monomer during the polymerization reaction to yield a suitable substrate (as defined below).

Figure 5:
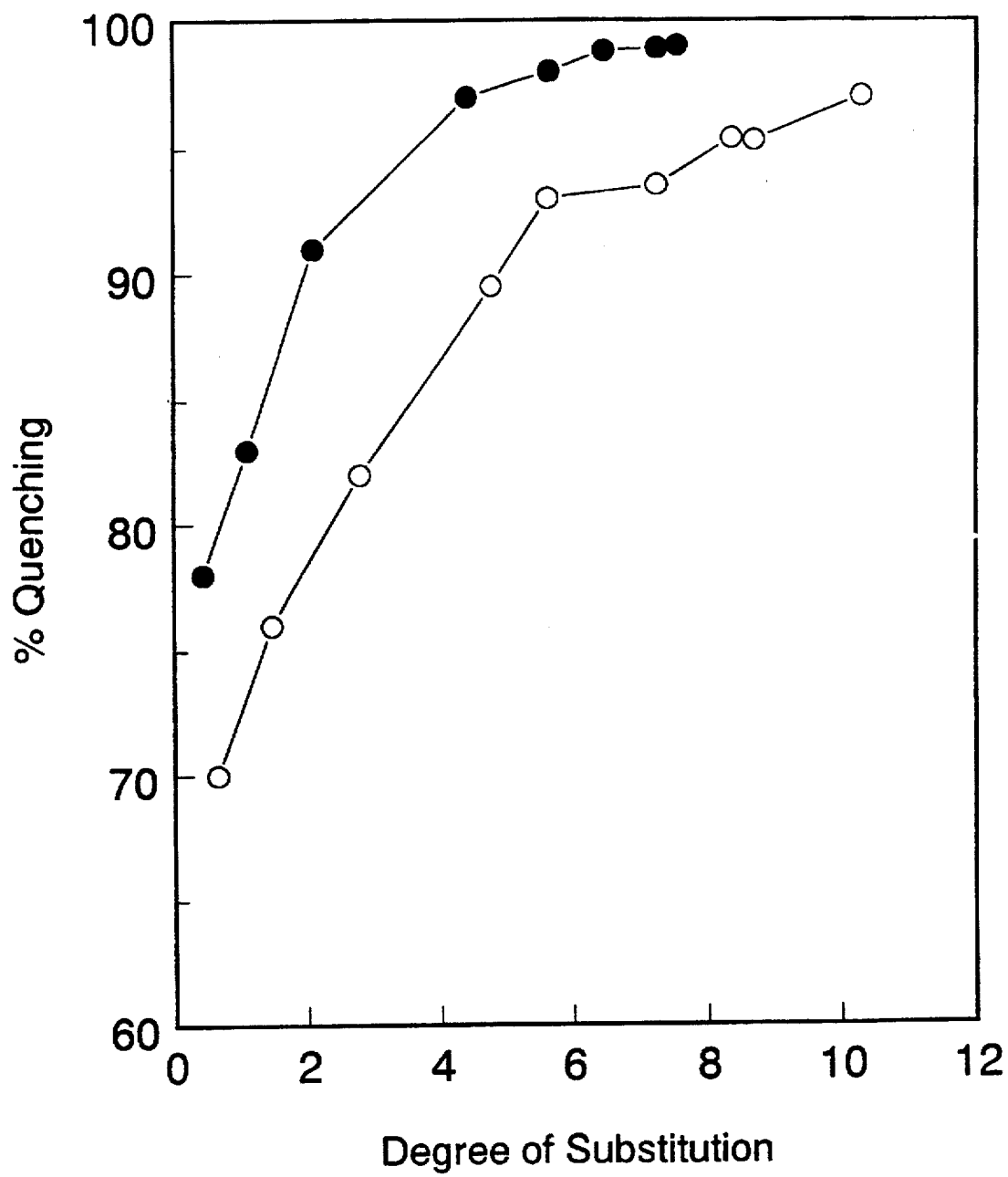
FIG. 5: The amount of fluorescence quenching achieved as a function of the degree of dye-substitution for a fluorescein-labeled casein (°) and a borapolyaza-s-indacene-labeled casein (•). Significantly greater quenching at lower degrees of substitution is observed for the borapolyaza-s-indacene-labeled substrate.
Figure 6:
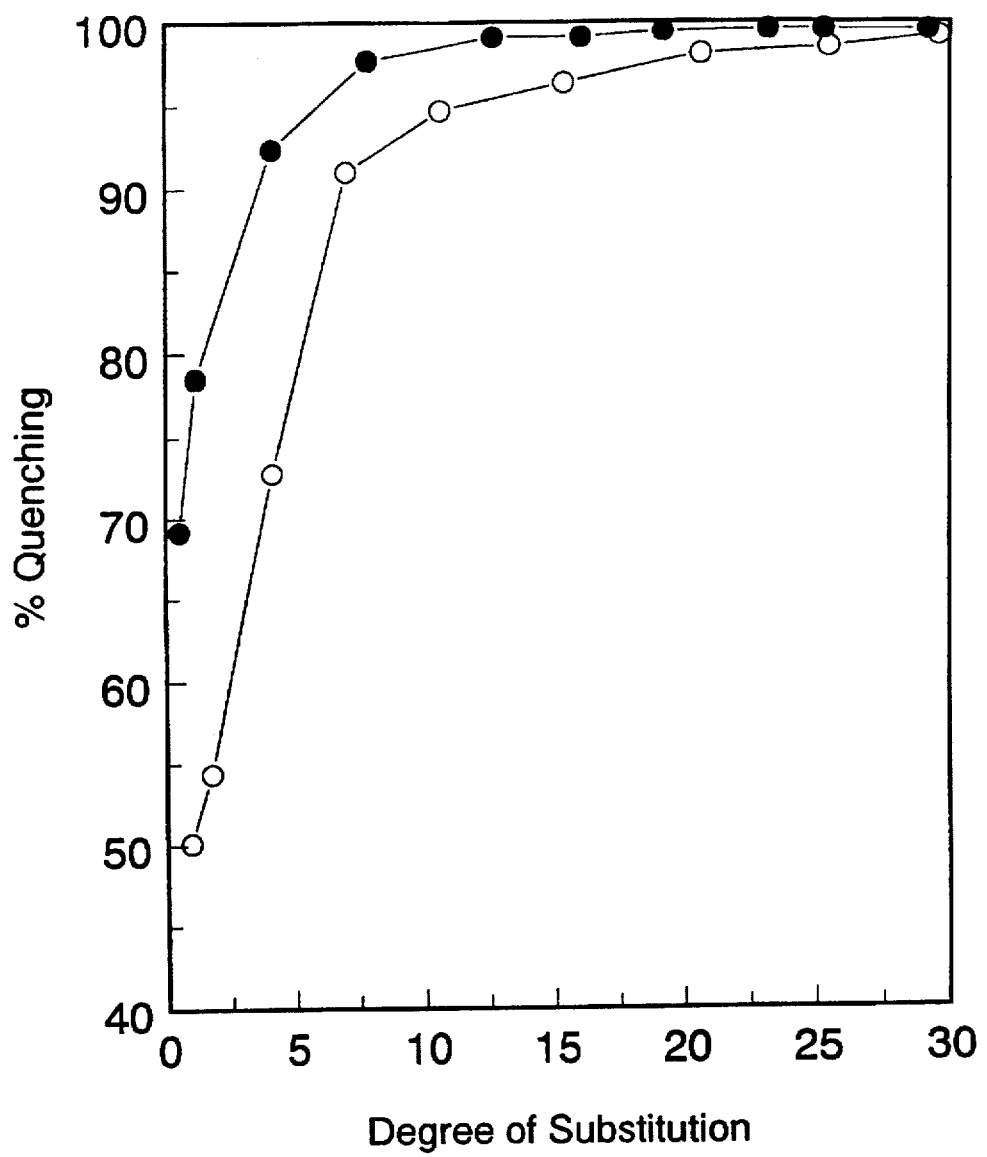
FIG. 6: The amount of fluorescence quenching achieved as a function of the degree of dye-substitution for a fluorescein-labeled BSA (°) and a borapolyaza-s-indacene-labeled BSA (•). Significantly greater quenching at lower degrees of substitution is observed for the borapolyaza-s-indacene-labeled substrate.
Figure 7:
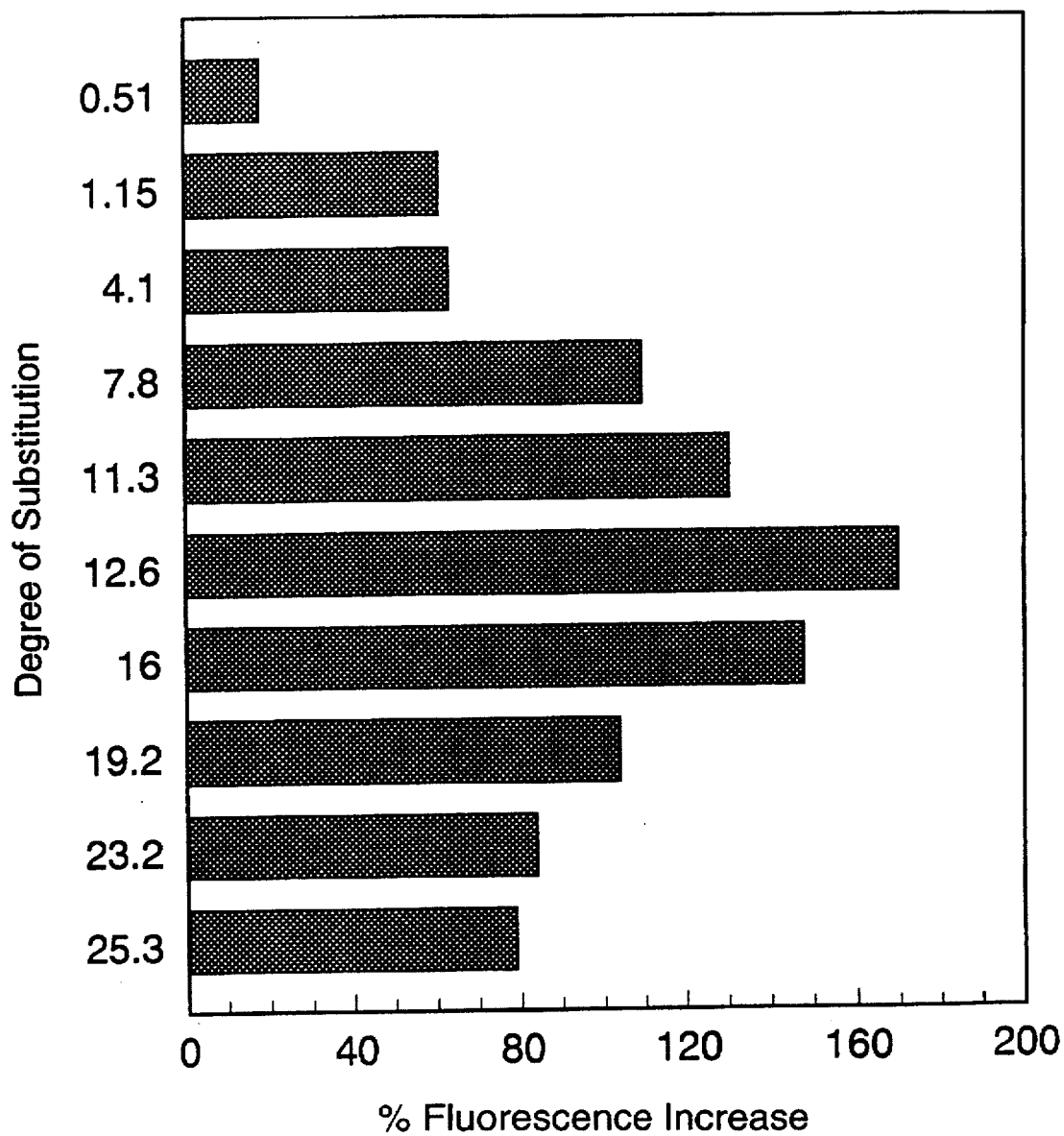
FIG. 7: The sensitivity of an assay for protease activity as a function of the degree of substitution of the quenched borapolyaza-s-indacene-labeled BSA that is the enzyme substrate. The assay sensitivity is determined by measuring the % increase in fluorescence upon degradation of the polymer.

The preferred labeled polymers used for this invention are those that show a high degree of quenching of the fluorescent dye(s) as the result of their attachment to the polymer and for which fluorescence is strongly enhanced by degradation of bonds within the polymer (e.g. enzymatic hydrolysis of the polymeric substrate). The labeled polymer will typically have an average of at least one dye per 10,000 daltons of mass but never less than two dyes per polymer, more typically at least 1.5–2.5 dyes per 10,000 daltons. Polymers having a lower molecular weight typically require greater degrees of substitution to yield useful results. Polymers having a molecular weight of <10,000 daltons are typically substituted by 2–3 dyes. Polymers having a molecular weight of 10,000–30,000 daltons are typically substituted by 3–6 dyes. Finally, polymers having a molecular weight that is ≧30,000 daltons are typically substituted by 1–2 dyes/10,000 daltons. Preferably, fluorescence of the dye-labeled polymer is quenched by at least 90% relative to the free, unconjugated form of the dye. More preferably the quenching of the labeled polymer is greater than 95% and most preferably greater than 98%. Although polymers labeled to a high degree tend to yield the greatest quenching, the tendency of some polymers to precipitate when labeled to a significant extent with the more hydrophobic dyes, or the tendency of a high degree of labeling to interfere with enzymatic interaction, may require fewer dyes per polymer and thus lower degrees of quenching (as shown in FIG. 7). Polymers whose fluorescence is quenched greater than about 50% are still useful for at least qualitative measurement of enzymatic activity, e.g. when used in a lower ratio of substrate to enzyme and/or when hydrolysis of the polymer proceeds to a point close to completion. In contrast to the use of xanthene-based dyes such as the fluoresceins, high degrees of quenching (>95%) are relatively easy to obtain using the preferred borapolyazaindacene dyes (as shown in FIGS. 5 and 6).

Assay

The assay of degradation activity comprises exposing the dye-labeled polymer to the degradation conditions of interest for a period of time sufficient for degradation to occur, followed by detecting the change in fluorescence. If the detecting step is conducted during the degradation activity, the assay is a continuous assay. Since most enzymes show some selectivity among substrates, and as that selectivity can be demonstrated by determining the kinetic differences in their hydrolyric rates, rapid testing for the presence and activity of the target enzyme is provided by the enhancement of fluorescence of the labeled substrate.

Where the degradation activity is enzymatic hydrolysis, the substrate is combined with the enzyme in a way that facilitates contact of the enzyme and its substrate under conditions suitable for substrate hydrolysis. By bringing the substrate and enzyme into contact is meant, for instance, mixing of a solution of the substrate with a sample that contains or is suspected of containing an enzyme or multiple enzymes. The enzyme used to practice the invention is optionally free in solution (including biological fluids or culture medium); enclosed within a biological structure (i.e. an organism or a discrete unit of an organism, including live or permeabilized cells); extracted from a biological structure (e.g. from lysed cells, tissues, organisms or organelles); or immobilized in or on a solid or semi-solid material or a membrane such as in an agar matrix or on a nylon membrane. Incorporation of the polymeric substrate in a matrix such as agar can be used to detect, for instance, secretion of enzymes from cells grown in the matrix. The substrate is typically added in the form of a solution but can also be immobilized on a carrier such as a natural or synthetic polymer or in a matrix such as agar, in which case the enzyme is usually in a soluble form. Typically the substrate is used in a molar excess to the enzyme; most typically this excess is at least 10-fold and frequently at least 100-fold.

The polymer is exposed to the degradation activity under conditions that allow the degradation to occur. For enzymatic activity, the substrate is combined with the enzyme under suitable conditions that allow for hydrolysis. By suitable conditions for enzymatic reaction is meant any condition that will permit hydrolysis to proceed to yield at least the minimum desirable fluorescence change. These conditions are strongly affected by temperature, pH and changes in composition of the medium. Most enzymes are functional at physiological temperature and pH, but may be affected by the presence or absence of co-factors or inhibitors and other features widely recognized by enzymologists. Suitable conditions for one enzyme may be unsuitable conditions for a different enzyme. The absence of a positive response (increase in fluorescence) is useful in determining the necessary conditions for the degradation activity to occur. Conditions of the enzymatic reaction can typically be adjusted to accelerate or decelerate the enzymatic reaction or to favor or hinder an enzymatic reaction, which changes may be useful for distinguishing among enzymes in a solution thought to contain multiple enzymes. For instance, the use of selective inhibitors such as inhibitors of cysteine proteases, serine proteases, metalloproteases and carboxypeptidases, in particular, can aid in distinguishing among classes of proteases.

The polymer is exposed to the degradation activity for the period of time neccesary to allow degradation to occur. The incubation period needed for an enzyme substrate is the amount of time required to determine the presence or absence of hydrolytic activity. Under most favorable conditions the time is less than one hour and may be as short as 1–10 minutes. However, the high chemical stability of the substrates permits them to be used to assay enzymes that have slow turnover rates and that require greater than one hour of incubation. Because hydrolysis typically results in a continuous increase in fluorescence intensity of the hydrolyzed polymer, the results can usually be monitored continuously over a period of time. Alteratively the results can be monitored by intermittent sampling of the reaction mixture.

To detect the change in fluorescence, the sample is illuminated at a wavelength that results in a detectable fluorescence response. The photons that are emitted are detected by eye, by photographic fill, by instrument, or by any other means capable of detecting fluorescence resulting from illumination of the substrate.

For a homogeneous solution of the enzyme and the substrate, fluorescence is typically detected by illumination of the substrate and sample with a light source capable of producing light that is absorbed at or near the wavelength of maximum absorption of the dye and fluorescence is detected at a wavelength longer than the excitation wavelength, typically near the emission maximum. This may be, for instance, a hand-held ultraviolet lamp, a lamp of a fluorometer, spectrofluorometer or fluorescence-detected microplate reader, a laser or laser diode or even sunlight. Because fluorescence that results from hydrolysis of the preferred polymeric substrates is preferably very low before hydrolysis, it is not necessary to precipitate or otherwise separate the polymeric substrate from its products before analysis, although this can be done if desired. Thus the assay does not require extensive manipulation of the materials and is fast and reproducible.

In the case of a sample in which either the substrate or the enzyme or both are immobilized or partially immobilized on a solid or semi-solid support or in a matrix such as agar, the fluorescence is typically detected using excitation by a transilluminator, an epi-illuminator, a laser scanner, a microscope or a similar apparatus that permits observation of the matrix.

Detection of fluorescence may use an instrument or be by visual inspection, optionally comprising photography of the sample. Fluorescence that results from localized hydrolysis of the fluorogenic substrate such as within a cell that phagocytoses the polymeric substrate is typically detected using instrumentation that is capable of detecting fluorescence in single cells such as a microscope or a flow cytometer (optionally further being followed by sorting of fluorescence-labeled cells). Alternatively, multiple cells are suspended and fluorescence changes are measured as for an assay done in true solution.

The degradation activity is frequently measured relative to a fluorescence standard of determined intensity. The standard may be a fluorescent dye such as the dye used to prepare the labeled polymer, a fluorescent particle (including fluorescent latex particles), a calibration curve prepared by assaying the substrate with a known amount of enzyme or degradation activity, or any other standard that can be used to calibrate fluorescence intensity as well known in the art.

When the assay is used to detect an enzyme that is within a cell or in an otherwise localized space, such as in an agar gel, or on a membrane, the detection of the hydrolytic product is optionally combined with a second detection reagent such as an antibody or a stain for another component of the system such as an organelle stain, or a probe to assess viability of the cell. The second detection reagent can be fluorescent labeled with a dye that has color contrasting with that of the substrate or with a label that is detectable by other optical or non-optical properties.

Enzymes

Enzymes to be analyzed include those from a wide variety of biological sources, including from animals, plants, bacteria and yeast, provided that they are able to hydrolyze chemical bonds within the labeled substrate. By hydrolysis of a chemical bond is meant the addition of the elements of water to at least one chemical bond found in the substrate. Commonly this bond is an amide or an ester or thioester of a carboxylic acid or phosphoric acid; or the chemical bond is an ether or a thioether. Typically the enzyme hydrolyzes a bond that is part of the primary structure (backbone) of the polymer, resulting in fragments that have significantly lower molecular weight. For example, hydrolysis of a protein may yield two or more separate peptides whose sum of molecular weights approximates that of the original protein. Different enzymes having different specificities typically yield different products from the same substrate and their changes in fluorescence intensities may also be different. Enzymes include biological molecules that have been modified either naturally or through chemical or genetic alteration to enhance or reduce their biological activity or selectivity, including enzymes from mutant strains, catalytic antibodies and ribozymes.

Among the most preferred enzymes are proteases, such as exopeptidases and endopeptidases, including serine, cysteine proteases, carboxypeptidases and metalloproteases. Their substrates are typically natural or synthetic peptides or proteins. Examples of useful proteases include chymotrypsin; trypsin; papain; falcipain; thrombin; plasmin (fibrinolysis); aureus protease; cathepsin A, B, D, E, F, G, H, L, M, S and other cathepsins; prolyl endopeptidase; kallikreins (including plasma, pancreatic or urine); pancreatic elastase and other elastases, including leukocyte elastase (lysosomal elastase); tissue plasminogen activator; subtilisin A (from *Bacillus licheniformis*) and other subtilisins; fiein; bromelain (stem bromelain); clostripain; calpain I and II and other calpains; kinase A; pepsin; lysosomal collagenase, tissue collagenase (including clostridiopeptidase A), and other collagenases; metalloendopeptidase (enkephalinase, enkephalinase A); renin; dynorphin converting enzyme; urokinase; aminopeptidases (aminoacylpeptide hydrolases), including cytosolic aminopeptidase (leucine aminopeptidase), aminopeptidase M or N (microsomal aminopeptidase; particle-bound aminopeptidase); cystylaminopeptidase (oxytocinase); proline aminopeptidase, and other aminopeptidases; aspartic proleinase; pronase; poliovirus C3 protease; proteinase K; HIV protease; pyroglutamate aminopeptidase; ingesin; macropain; meprin; pectinase; serine, proline, and tyrosine carboxypeptidase, and other carboxypeptidases.

Glycosidase enzymes include β-galactosidase (EC 3.2.1.23), α-galactosidase (EC 3.2.1.22), β-glucuronidase (EC 3.2.1.31 ), N-acetyl-β-galactosaminidase (EC 3.2.1.30), α-glueosidase (EC 3.2.1.20), β-glucosidase/glucocerebrosidase (EC 3.2.1.21 ), N-acetyl-β-glucosaminidase (hexosaminidase) (EC 3.2.1.30), N-acetyl-α-glucosaminidase, marmosidase II, α-iduronidase, α-mannosidase, neuraminidase (α-NAGase), β-fucosidase, and cellulase.

The presence of the enzyme may be indicative of different metabolic or disease states. For example, one of most important means for tumor cell invasion is to destroy the intercellular matrix by release of various proteases. In one aspect of the invention, the proteases released from tumor cells hydrolyze the immobilized substrate, yielding enhanced fluorescence (Example 12). Similarly, the enhanced fluorescence indicates the process of transformation when the carcinogen or oncogene-treated cells are cultured on such a medium. In another aspect of the invention, fluorogenic polymer substrates are used to monitor phagocytosis (Example 10).

Labeled Polymers as Detection Reagents

In one embodiment, the labeled polymer is additionally covalently attached to a member of a specific binding pair, and is used as a probe for the complementary member of that specific binding pair. A specific binding pair member can be a ligand or a receptor. As used in this document, the term ligand means any organic compound for which a receptor naturally exists or can be prepared. A receptor is any compound or composition capable of recognizing a spatial or polar organization of a molecule, e.g. epitopic or determinant site. Ligands for which naturally occurring receptors exist include natural and synthetic proteins, including avidin and streptavidin, antibodies, enzymes, and hormones; nucleotides and natural or synthetic oligonucleotides, including primers for RNA and single- and double-stranded DNA; polysaccharides and carbohydrates. Ligands and receptors are complementary members of a specific binding pair, each specific binding pair member having an area on the surface or in a cavity that specifically binds to and is complementary with a particular spatial and polar organization of the other. Representative specific binding pairs are shown in Table 2.

TABLE 2

| Representative Specific Binding Pairs | |
|---|---|
| antigen | antibody |
| biotin | avidin (or streptavidin) |
| IgG* | protein A or protein G |
| drug receptor | drug |
| toxin receptor | toxin |
| carbohydrate | lectin |
| peptide receptor | peptide |
| protein receptor | protein |
| carbohydrate receptor | carbohydrate |
| DNA (RNA) | aDNA (aRNA)† |
| enzyme | substrate |

*IgG is an immunoglobulin
†aDNA and aRNA are the antisense (complementary) strands used for hybridization In one aspect of the invention, the specific binding pair member is an antibody or antibody fragment, avidin or streptavidin. In this embodiment of the invention, the complementary binding pair member is typically a hapten, an antigen or a biotin. Where the complementary binding pair member is a hapten, the hapten typically has a molecular weight less than 1,000 daltons. In another aspect of the invention, the specific binding pair member is an oligonucleotide or nucleic acid polymer. Optionally, the complementary binding pair member is present in a cell, bacteria, virus or yeast cell such as an Fc receptor (Example 10). Alternatively, the complementary member is immobilized on a solid or semi-solid surface, such as a polymer, polymeric membrane (such as polyvinylidene difluoride or nitrocellulose) or polymeric particle (such as a microsphere), or in a semi-solid matrix (such as an electrophoretic gel).

Alternatively, multiple specific binding pair members may be sequentially linked to the labeled polymer, the complementary member, or to both, resulting in a series of specific binding pairs interposed between the labeled polymer and the analyte of interest. Table 3 shows the representative examples of specific binding complexes with and without additional specific binding pairs interposed between the labeled polymer and the analyte.

and semi-quantitating specific species of proteins, RNAs or DNAs. For example, the dot-blot experiments include immobilization of proteins or nucleic acids on membranes

TABLE 3

Representative Specific Binding Complexes

| ANALYTE | ADDITIONAL PAIRS | | | COMPLEMENTARY CONJUGATE |
|---|---|---|---|---|
| DNA | aDNA—biotin | avidin | | biotin—polymer |
| DNA | aDNA—antigen | antibody—biotin | avidin | biotin—polymer |
| DNA | | | | aDNA—polymer |
| DNA | aDNA—biotin | | | avidin—polymer |
| DNA | aDNA—hapten* | | | anti-hapten—polymer |
| RNA | aRNA—hapten* | | | anti-hapten—polymer |
| RNA | aDNA—biotin | | | avidin—polymer |
| antigen | mouse antibody | anti-mouse—biotin | | avidin—polymer |
| antigen | mouse antibody | anti-mouse | mouse anti-enzyme | enzyme—polymer |
| antigen | | | | antibody—polymer |
| antigen | antibody—hapten* | | | anti-hapten—polymer |
| carbohydrate | lectin—biotin | | | avidin—polymer |
| receptor‡ | ligand—biotin | | | anti-biotin—polymer |
| IgG | protein A—hapten* | | | anti-hapten—polymer |

‡for instance a drug receptor, a toxin receptor, peptide receptor, protein receptor or carbohydrate receptor
— is a covalent bond between two reagents; all other bonds are noncovalent Typically, a suitably labeled polymer is covalently bound to a member of a specific binding pair and used to label a sample that contains or is thought to contain the complementary member of the specific binding pair. Sufficient time is allowed for the two members of the specific binding pair to form a complex, the nature of said complex being dependent upon the type of specific binding pair utilized, but is typically characterized as non-covalent (i.e. Van der Waals and ionic) interaction. Unbound labeled polymer is removed from the sample by washing or rinsing the sample, and the substrate is then degraded. Typically the polymer is degraded by the addition of an appropriate enzyme to the sample, but the labeled polymer is optionally exposed to any condition that results in degradation of the polymer, such as chemical treatment with chaotropic agents, heat treatment, ionizing radiation, mechanical force, photolysis, sound, untrasound, drug interactions, changes in ionic strength, applied pressure, or exposure to organic solvents. The appearance of fluorescent degradation products in the sample indicates the presence and optionally the location of the complementary binding pair member. After sufficient time has elapsed, the sample is observed for a fluorescent signal to indicate localization of the fluorescent conjugate.

While the resulting fluorescent degradation products are readily detectable, the present invention is typically most useful when used to confirm the presence or absence of the analyte of interest in the sample. While the location of the analyte can be determined within the sample, localization of the analyte is only possible under conditions wherein the fluorescent degradation products are unable to substantially diffuse away from the location of the analyte prior to observation, such as where the sample medium is particularly viscous, or where the sample is contained in a sealed system, such as, for example, within a cell, in an agar gel, on a membrane or other solid or semi-solid matrix, in a cuvette or in a microplate well. In these instances, the diffusion of the fluorescent degradation products into the surrounding aqueous medium can be useful, such as in the case where the labeled polymer is used to detect analytes immobilized in the well of a microplate.

The labeled polymers are useful for enzyme-mediated methods used in standard blotting techniques for identifying followed by specific detection by antibody-enzyme or avidin-enzyme conjugates along with the labeled polymer. For the nucleic acid dot blot, the immobilized nucleic acid is allowed to hybridize with biotin-labeled complementary DNA or KNA probes before applying the labeled polymer-avidin, or -streptavidin conjugates, washing, and treating the blot with an appropriate enzyme selected to hydrolyze the labeled polymer. Similarly, the labeled polymers of the present invention are useful detection reagents for Western, Northern, and Southern blots, which are designed to specifically recognize proteins and nucleic acids following electrophoretic separation.

The examples below are given so as to illustrate the practice of this invention. They are not intended to limit or define the entire scope of this invention.

EXAMPLE 1

Preparation of a fluorogenic-protein substrate

Casein (17 mL of 5.9 mg/mL) in 0.3 M sodium carbonate buffer, pH 9.0, is treated with 4,4-difluoro-5,7-dimethyl-4-bora-3a,4a-diaza-s-indacene-3-propionic acid, succinimidyl ester (1.92 mL of 25 mg/mL in DMSO) (Molecular Probes, Inc. Eugene, Oreg.) for 90 minutes at room temperature. The orange-colored protein conjugate is separated from residual dye by chromatography on Sephadex G-25. The degree of substitution is calculated from the absorbance of the dye at 503 nm using an extinction coefficient of 68,000 $cm^{-1}M^{-1}$ and from the absorption of the protein at 280 nm following correction for the dye's absorption at 280 nm. The average degree of dye substitution of the product (POLYMERIC PROTEASE SUBSTRATE 1) is approximately 5.5 dyes per molecule of protein.

POLYMERIC PROTEASE SUBSTRATE 2, also with a degree of substitution between 5 and 6 molecules of dye per molecule of protein, is prepared similarly from casein and 6-((4,4-difluoro-5-(2-thienyl)-4-bora-3a,4a-diaza-s-indacene-3-yl)phenoxy)acetyl)aminohexanoic acid, succinimidyl ester) (Molecular Probes, Inc.).

EXAMPLE 2

Determination of quenching

Solutions of POLYMERIC PROTEASE SUBSTRATE 1 and the reference compound 4,4-difluoro-5,7-dimethyl-4- bora-3a,4a-diaza-s-indacene-3-propionic acid are prepared to the same optical density at 503 rim. The samples are diluted to an optical density of <0.02 and excited at 503 nm using an SPF-500™ spectrofluorimeter. The fluorescence intensity of the POLYMERIC PROTEASE SUBSTRATE 1 is compared with the reference compound measured with the same sensitivity. The measurements show that the relative fluorescence of the POLYMERIC PROTEASE SUBSTRATE 1 measured at 5 12 nm is less than 2–4% that of the reference compound. Similar measurements are made with similar quenching efficiencies using the POLYMERIC PROTEASE SUBSTRATE 2 using 590 nm excitation and 618 nm emission for the comparison.

EXAMPLE 3

Sensitivity of fluorogenic-protein substrate

A solution of POLYMERIC PROTEASE SUBSTRATE 1 is prepared at 1.0 mg/mL in water and diluted to 10 μg/mL in 1X Digestion Buffer (10 mM Tris-HCl, pH 7.8). Stock solutions from lyophilized enzymes are prepared at 1 mg/mL in glass vials as follows: pepsin in 0.01 M HCl; trypsin and α-chymotrypsin in 0.001 M HCl; Pseudomonas aeruquosa elastase (PAE), thermolysin, papain and cathepsin D in water. Human leukocyte elastase is prepared from 1 unit/mL in 10 mM Tris-HCl+1 mM EDTA, pH 7.5. Elastase from porcine pancreas was supplied in solution. All enzymes are serially diluted from the stock solution into optimal pH buffer for each enzyme in 1.6 mL Eppendorf tubes: pepsin in 10 mM HCl, pH 2.0; trypsin, α-chymotrypsin and thermolysin in 10 mM Tris-HCl, pH 7.8; PAE in 20 mM sodium phosphate, pH 8.0; papain in 10 mM MES, pH 6.2; human leukocyte elastase in Tris-HCl+1 mM EDTA, pH 7.5; porcine pancreas elastase in 10 mM Tris-HCl, pH 8.8, and cathepsin D in 20 mM sodium acetate, pH 5.0.

100 μL aliquots of each enzyme dilution series are placed in a Corning 96 U-well microplate and 100 of either POLYMERIC PROTEASE SUBSTRATE 1 or POLYMERIC PROTEASE SUBSTRATE 2 is added to each well. Thus, the enzyme concentrations range from 0.025 ng/mL to 5 μg/mL with 5 μg/mL of the POLYMERIC PROTEASE SUBSTRATE. The microplates are incubated for 1 hour at room temperature with protection from light. Sample fluorescence is measured in a CytoFluor 2300 fluorescence microplate reader (Perseptive BioSystems) using a 485 nm excitation filter and a 530 nm emission filter for POLYMERIC PROTEASE SUBSTRATE 1 or an 590 nm excitation filter and 645 nm emission filter for POLYMERIC PROTEASE SUBSTRATE 2. Fluorescence emission versus enzyme concentration is plotted, and limits of detection are determined. The detection limits are defined as the amount of enzyme required to cause a 10% change in fluorescence compared to the control sample at room temperature. Detection limits are reported in standard enzyme activity units as defined by the enzyme's supplier, after conversion from concentration units. Results are shown in Table 4.

TABLE 4

Detection limits of protease substrates at 22° C.

| Enzyme | Class | Detection Limit (Units) | Buffer Conditions |
|---|---|---|---|
| Elastase Type IV | Serine Protease | $2.2 \times 10^{-3}$ | 10 mM Tris-HCl, pH 8.8 |

TABLE 4-continued

Detection limits of protease substrates at 22° C.

| Enzyme | Class | Detection Limit (Units) | Buffer Conditions |
|---|---|---|---|
| porcine pancreas Chymotrypsin Type II | Serine Protease | $5.0 \times 10^{-5}$ | 10 mM Tris-HCl, pH 7.8 |
| bovine pancreas Thermolysin B. proteolyticus rokko | Acid Protease | $4.4 \times 10^{-5}$ | 10 mM Tris-HCl, pH 7.8 |
| Trypsin Type IX porcine pancreas | Serine Protease | $1.3 \times 10^{-2}$ | 10 mM Tris-HCl, pH 7.8 |
| Papain papaya latex | Sulfhydryl Protease | $2.1 \times 10^{-4}$ | 10 mM MES, pH 6.2 |
| Pepsin, porcine stomach mucosa | Acid Protease | $2.1 \times 10^{-3}$ | 10 mM HCl, pH 2.0 |
| Pseudomonas aeruquosa elastase (PAE) | Serine Protease | $1.0 \times 10^{-3}$ | 20 mM sodium phosphate, pH 8.0 |
| Human leukocyte elastase | Serine Protease | $1.0 \times 10^{-3}$ | 10 mM TE, pH 7.5 |
| Cathepsin D | Acid Protease | $5.0 \times 10^{-5}$ | 20 mM sodium acetate, pH 5.0 |

The detection limit is defined as the amount of enzyme required to cause a 10–20% change in fluorescence compared to the control sample at 22° C. Enzyme unit definitions are standard definitions for each individual enzyme. Detection limits may vary with instrumentation.

Fluorescence measurements made in 1-cm cuvettes using a spectrofluorimeter require at least a 10-fold increase in the volume and show similar results. Comparison of results using the highly quenched POLYMERIC PROTEASE SUBSTRATE 1 with fluorescein-labeled casein with a lesser degree of substitution (as described in Bolger, et al. supra) shows an increase in sensitivity to proteases with the greater degree of substitution.

EXAMPLE 4

Standard curve generation

Figure 2:
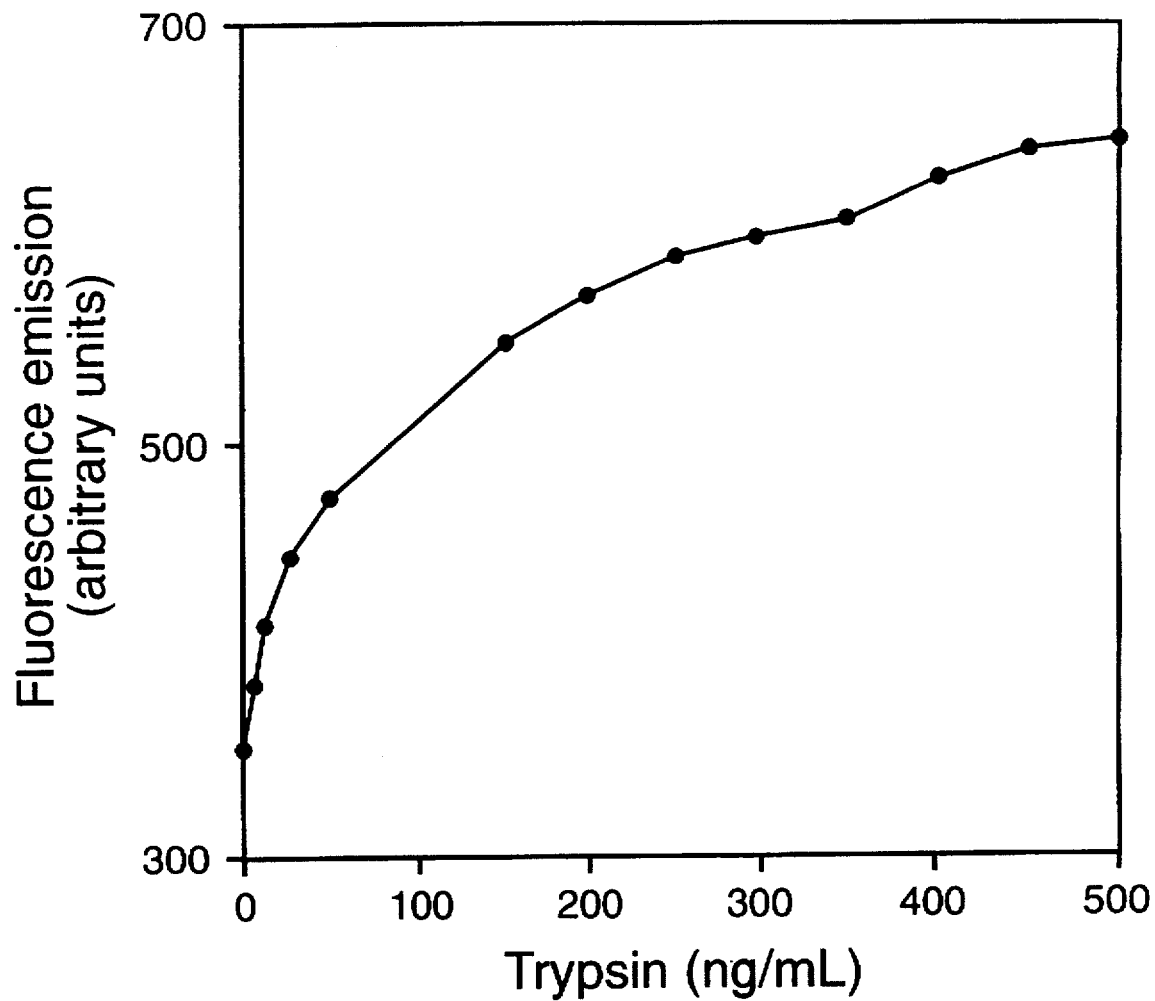
FIGS. 2: A sample standard curve obtained with the polymeric protease substrate as described in Example 4. Fluorescence emission at 530 nm versus trypsin concentration (ng/mL) is plotted using linear methods.

To quantitate the activity of purified protease preparations, a protease activity standard curve is generated. If possible, an appropriate enzyme standard of known specific activity that closely matches the protease activity being determined is used. Protease activity is expressed as fluorescence change per unit sample. A standard curve is generated for the POLYMERIC PROTEASE SUBSTRATE 1 and trypsin by incubating a variable amount of the enzyme with a constant amount of substrate using the conditions described in Example 3. Plotting fluorescence versus protease activity using the full log, semi log, or linear method gives a standard curve. Results are shown in FIG. 2. Sensitivity is increased by incubating for up to 24 hours. Standard curves vary with enzyme type.

EXAMPLE 5

Time course of an enzymatic reaction

Figure 3:
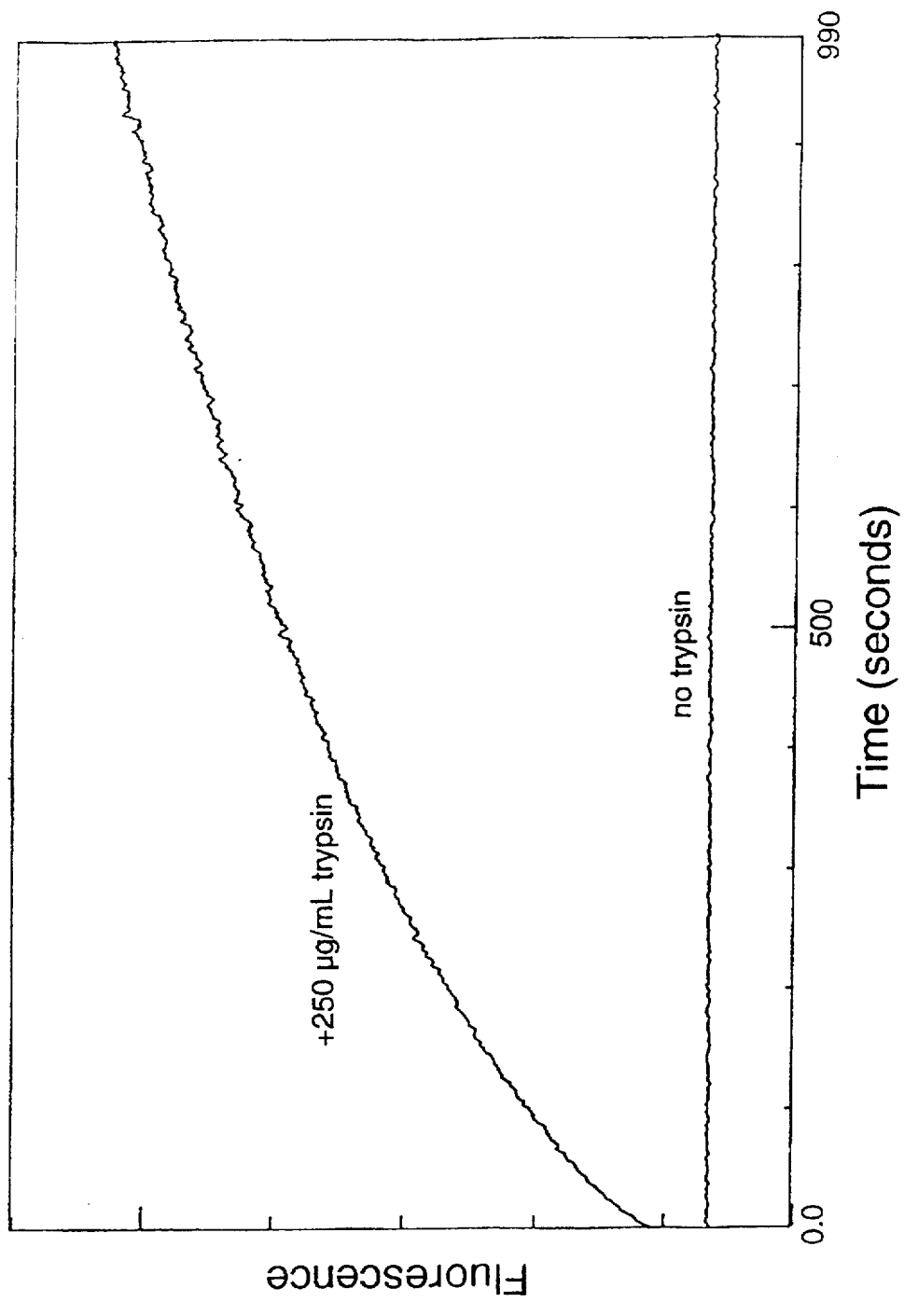
FIG. 3: Time course of an enzymatic degradation of a fluorogenic polymeric substrate as described in Example 5.
Figure 4:
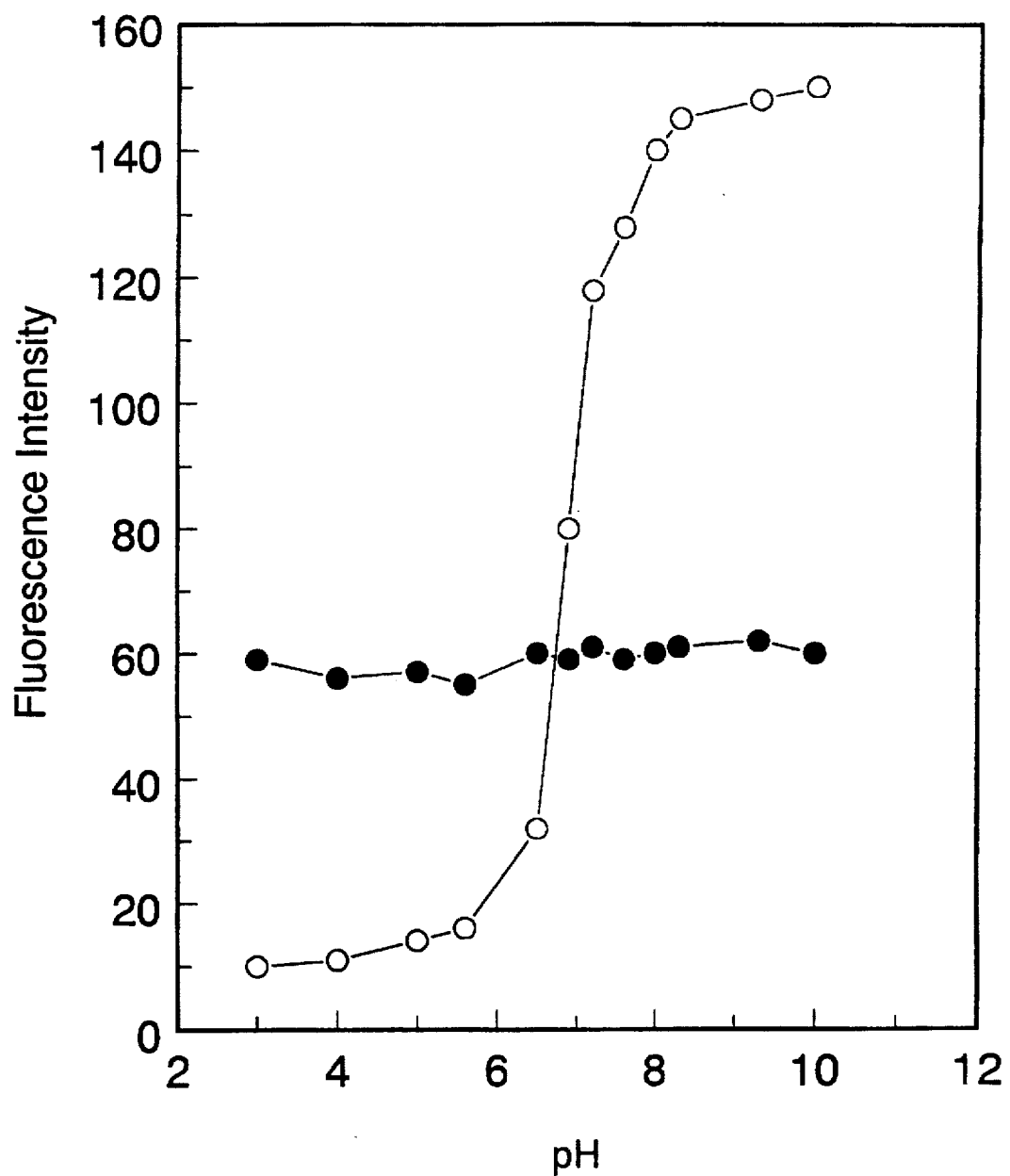
FIG. 4: The sensitivity of fluorescence intensity to pH demonstrated by a fluorescein conjugate of bovine serum albumin, or BSA, (°), compared to the insensitivity to pH effects demonstrated by a borapolyaza-s-indacene conjugate of BSA (•) (prepared as in Example 8).

Continuous measurement of the turnover of POLYMERIC PROTEASE SUBSTRATE 1 by trypsin is accomplished by incubating 5/μg/mL of substrate in TE, pH 7.5 with 250/μg/mL trypsin as described in Example 2 except with 20-times the volume of reactants. Rather than making a single fluorescence measurement at one hour, fluorescence of the sample is continuously detected using an SFP-500™ spectrofluorimeter (Ex 480 nm; Em 514 nm; slits 2/4; HV=1200). The results are shown in FIG. 3.

EXAMPLE 6

Preparation of a fluorogenic-polysaccharide substrate

Amino dextran (Molecular Probes, Inc., Eugene, Oreg.) with an average molecular weight of 70,000 daltons and an average of 15.5 amines per dextran (10 mL of 10 mg/mL) is treated with 1.7 mL of a 10 mg/mL solution of 4,4-difluoro-5,7-dimethyl-4-bora-3 a,4a-diaza-s-indacene-3-propionic acid, succinimidyl ester in DMSO. After one hour, the residual dye is removed by chromatography on Sephadex G-25. Following lyophilization, the degree of substitution of the dextran is determined by measuring the absorbance of a solution of the conjugate (POLYMERIC DEXTRANASE SUBSTRATE 1) at 503 nm, using an extinction coefficient for the dye of 68,000 $cm^{-1}M^{-1}$ and the known weight of the product. The substrate prepared by this method contains approximately 12 dyes per average dextran molecule. Quenching of the fluorescence of the POLYMERIC DEXTRANASE SUBSTRATE 1 relative to 4,4-difluoro-5,7-dimethyl-4-bora-3a,4a-diaza-s-indacene-3-propionic acid is determined as described in Example 2 to be greater than 95%.

EXAMPLE 7

Sensitivity of a fluorogenic-polysaccharide substrate

The POLYMERIC DEXTRANASE SUBSTRATE 1 is dissolved at 0.4 mg/mL in 0.1 M sodium citrate, pH 6.0 buffer. Dextranase Penicllium sp. (Worthington Biochemical Co., Freehold, N.J.) is prepared in the same buffer at serial dilution to generate enzyme concentrations of $10^{-5}$ to 0.1 unit per 100 µL. Each 100 µL of substrate (40 µg) is combined with 100 µL of enzyme dilution in a microplate well and incubated for 1 hour at 22 ° C. The sensitivity of the assay is determined to be $2\times10^{-4}$ units.

EXAMPLE 8

Preparation of a fluorogenic substrate from bovine serum albumin

Bovine serum albumin (BSA; 15 mg/mL) in 0.2 sodium carbonate buffer, pH 9.0 is treated with 4,4-difluoro-5,7-dimethyl-4-bora-3a,4a-diaza-s-indacene-3-propionic acid, succinimidyl ester in DMSO at molar ratio of 1:30. Following incubation for 60 minutes, the conjugate (POLYMERIC PROTEASE SUBSTRATE 3) is purified by chromatography on Sephadex G-25. The degree of substitution is determined as described in Example 1 to be approximately 12 dyes per molecule of BSA and the quenching is determined as described in Example 3 to be greater than 98%. POLYMERIC PROTEASE SUBSTRATE 4, also with a degree of substitution between 5 and 6 molecules of dye per molecule, is prepared similarly from BSA and 4,4-difluoro-5-(2-pyrrolyl)-4-bora-3a,4a-diaza-s-indacene-3-propionic acid, succinimidyl ester) (Molecular Probes, Inc.).

EXAMPLE 9

Use of a polymeric substrate to detect proteases from neutrophils by fluorescence imaging Human neutrophils are incubated on a glass surface coated with 5 µg/mL of POLYMERIC PROTEASE SUBSTRATE 3. Following stimulation with phorbol myristate acetate (PMA), neutrophils release proteases in circular zones at adherence sites. These pericellular proteases cleave the surface-bound substrates, yielding the enhanced fluorescent image. Alternatively, the adherent neutrophils are covered with a thin layer of low-melting agarose containing 5 µg/mL of POLYMERIC PROTEASE SUBSTRATE 3 and 100 ng/mL of PMA stimulus. Following incubation at 37 ° C., microscopic examination reveals the enhanced fluorescence around the cells, indicating the proteolytic activity of activated neutrophils.

EXAMPLE 10

Use of a polymeric substrate to measure phagocytosis in neutrophils by flow cytometry Opsonized natural ocurring particles, such as bacteria., yeasts, and artificial particles, such as latex beads and zymosans, are the targets of phagocytosis. Heat-killed bacteria are opsonized with 1:50 dilution of anti-bacteria IgG at 4 ° C. for 30 min and washed with phosphate-buffered saline (PBS). The opsonized bacteria are coated with 5 µg/mL of POLYMERIC PROTEASE SUBSTRATE 3 in PBS at 4° C. for 30 min, and then washed with PBS. Following incubation with human neutrophils, the bacteria are internalized into neutrophils by Fc receptor-mediated phagocytosis. The quenched substrates on the internalized bacteria are subjected to the hydrolysis of proteases in the phagovacuole, yielding enhanced fluorescence. The intensity of enhanced fluorescence is used to measure the index of phagocytosis (number of targets in 100 neutrophils).

EXAMPLE 11

Use of a polymeric substrate to detect Fc receptor-activated intracellular elastase POLYMERIC PROTEASE SUBSTRATE 3 reacts with rabbit anti-BSA IgG at the ratio of equivalence to form insoluble immune complexes. Following incubation with human neutrophils at 4° C. for 30 minutes, then at 37° C., the immune complexes are internalized into phagosomes, and hydrolyzed by elastase, yielding enhanced fluorescence measured by flow cytometry. The time-dependent fluorescent increase reveals the kinetics of phagocytosis and protease activation.

EXAMPLE 12

Use of a polymeric substrate to characterize tumor cell invasion and monitor cell transformation A semi-solid agarose medium is prepared by mixing sterilized 2% agar with 2X D-MEM medium with POLYMERIC PROTEASE SUBSTRATE 3 to give a final agar concentration of 0.9% and substrate concentration of 5 µg/mL. The mixture of medium and substrate is poured into 24-well polystyrene culture plates. The plates are allowed to solidify at 4° C. for 60 minutes. A solution of 0.29% agar containing the desired concentration of tumor cells is added to the plates to give a final cell concentration of 2,000 cells per well. The plates are cultured at 37° C. for three days. The appearance of fluorescence around the cells under a 360 UV lamp is used to indicate the proteolytic activity of the cultured cells.

EXAMPLE 13

Use of a polymeric substrate to detect subtilisin excretion by *Bacilllus subtilis*

A solution of low-melting temperature agarose in minimal salts solution is sterilized by autoclaving and subsequently cooled. While the agarose solution is still liquid, enough of a filter-sterilized POLYMERIC PROTEASE SUBSTRATE 1 stock solution is added to result in a final concentration of 1 mg/mL POLYMERIC PROTEASE SUBSTRATE 1. The agarose mixture is then poured into 60 mm polystyrene culture dishes and cooled to 5° C. to promote solidification. Plates are allowed to dry for 1 day. Five 4 mm diameter, equally-spaced wells are cut in the agarose in each plate with a sterile punch. Suspensions of stationary-phase Bacillus subtilis bacteria in minimal salts solution containing ten-fold dilutions of between $1 \times 10^4$ and $1 \times 10^8$ cfu/mL are pipeted into the wells to fill them completely. The plates are covered, sealed, and incubated at room temperature for several days. The development of halos of fluorescence around the wells is observed by removing of the cover and illuminating with a 360 nm UV lamp. The diameter of each green fluorescent halo is indicative of the amount of active protease that has been released by the bacteria.

Example 14

Use of a polymeric substrate to screen extracellular proteolytic activity of soil microbes One gram samples of soil are obtained aseptically and suspended by vortexing in 10 mL of sterile distilled water. The suspensions are subjected to centrifugation at 250 Xg for 10 minutes and the supernatant solution is reserved. The supernatant solution is processed through a series of 6 ten-fold dilutions, and 0.1 mL of each dilution is plated onto a 100 mm petri plate of nutrient agar. Following incubation at room temperature for two days, isolated bacterial colonies are picked with a sterile needle, inoculated into sterile 0.2% tryptone broth, and the cultures incubated for 24 hours at room temperature. Bacteria are subsequently removed from the culture medium by centrifugation at 10,000 Xg for 15 minutes. The supernatants are removed and split into two samples. One sample is boiled for 10 minutes while the other is kept on ice. Enough of a sterile solution of POLYMERIC PROTEASE SUBSTRATE 1 is added to both samples to yield a final concentration of 1 mg/mL POLYMERIC PROTEASE SUBSTRATE 1 and the sample fluorescence is measured in a fluorescence microplate reader equipped with a 485 nm excitation filter and 520 nm emission filter. Measurements of fluorescence are made over 2–3 hours to detect protease activity in the samples.

It is to be understood that, while the foregoing invention has been described in detail by way of illustration and example, numerous modifications, substitutions, and alterations are possible without departing from the spirit and scope of the invention as described in the following claims.

What is claimed is:

1. A polymer having a molecular weight that is greater than or equal to 5,000 daltons, having conjugated thereto at least 2 molecules of a borapolyaza-s-indacene dye wherein the conjugated dye on the polymer exhibits fluorescence quenching of greater than 95% relative to the borapolyaza-s-indacene dye that is unconjugated.

2. A polymer, as claimed in claim 1, that is a peptide, protein, polysaccharide, oligonucleotide or nucleic acid.

3. A polymer, as claimed in claim 2, having a molecular weight of at least 20,000 daltons.

4. A polymer, as claimed in claim 3, that is an albumin or a casein.

5. A polymer, as claimed in claim 3, that is a collagen or a fibronectin.

6. A polymer, as claimed in claim 1 that is a polysaccharide.

7. A polymer, as claimed in claim 6, that is a dextran, an agarose, a cellulose, a polysucrose, a heparin, a glycogen, an amylopectin, a mannan, an inulin, or a starch.

8. A polymer, as claimed in claim 1, that is a ribonucleic acid or a deoxyribonucleic acid.

9. A polymer, as claimed in claim 1, wherein the dye has the structure

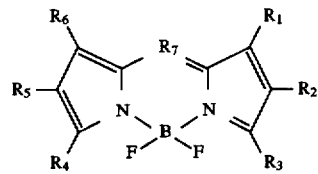

wherein the dye is attached to the polymer at one of $R_1$–$R_7$; and for the remainder of $R_1$–$R_7$ at which the polymer is not attached:

$R_1$, $R_2$, $R_3$, $R_4$, $R_5$ and $R_6$, which may be the same or different, are hydrogen, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or aryl or heteroaryl; or adjacent substituents $R_1$ and $R_2$, and adjacent substituents $R_5$ and $R_6$, when taken in combination form a fused benzo ring that is optionally substituted by hydrogen, halogen, nitro, sulfo, cyano, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons; or substituted or unsubstituted aryl, heteroaryl, aryl-amido, heteroarylamido, aryl-oxy, heteroaryl-oxy, aryl-amino, or heteroaryl-amino; or the one or more fused benzo rings are substituted by 1–2 additional fused benzo or heteroaromatic rings;

$R_7$ is nitrogen; or methine; or halogen-, cyano-, alkyl-, perfluoroalkyl-, alkoxy-, alkenyl-, alkynyl-, cycloalkyl-, arylalkyl-, acyl-substituted methine wherein the alkyl portions of each contain fewer than 20 carbons; or aryl- or heteroaryl-substituted methine.

10. A polymer, as claimed in claim 9, wherein the dye is a 4,4-difluoro-4-bora-3a,4a-diaza-s-indacene.

11. A polymer, as claimed in claim 10, that is a peptide, protein, polysaccharide, oligonucleotide or nucleic acid.

12. A polymer, as claimed in claim 11, that has a molecular weight of at least 20,000 daltons.

13. A polymer, as claimed in claim 12, that is a protein.

14. A polymer, as claimed in claim 1, further comprising a covalently attached member of a specific binding pair.

15. A method of detecting the degradation of a polymer having a molecular weight of at least 5,000 daltons, comprising:

a) preparing a labeled polymer having conjugated thereto at least 2 molecules of a borapolyaza-s-indacene dye, wherein the conjugated dye exhibits fluorescence quenching of at least 90% relative to the borapolyaza-s-indacene dye that is unconjugated;

b) exposing a sample of the labeled polymer to a condition that is suspected will decade the labeled polymer for a time sufficient to degrade the polymer;

c) comparing the fluorescence of the exposed sample to a fluorescence standard of determined intensity; and d) correlating the fluorescence of the exposed sample to the degradation of the polymer.

16. A method, according to claim 15, wherein the conjugated dye exhibits fluorescence quenching of at least 98% relative to the borapolyaza-s-indacene dye that is unconjugated.

17. A method, according to claim 15, wherein the labeled polymer is a peptide, protein, polysaccharide, oligonucleotide or nucleic acid.

18. A method, according to claim 17, wherein the labeled polymer is immobilized in or on a solid or semi-solid matrix.

19. A method, according to claim 17, wherein the labeled polymer has a molecular weight of at least 20,000 daltons.

20. A method, according to claim 17, wherein the labeled polymer is a protein.

21. A method, according to claim 10, wherein the protein is an albumin or a casein.

22. A method, according to claim 15, wherein the condition is the presence of an enzyme.

23. A method, according to claim 22, wherein the enzyme is present in a solution, within a biological structure, extracted from a biological structure, or immobilized in or on a solid or semi-solid matrix.

24. A method, according to claim 23, wherein the enzyme is present in a biological fluid or a culture medium.

25. A method, according to claim 23, wherein the enzyme is within a live or permeabilized cell.

26. A method, according to claim 23, wherein the enzyme is secreted by or extracted from cells, tissues, organisms or organelles.

27. A method, according to claim 23, wherein the enzyme is immobilized in or on an agar matrix or a membrane.

28. A method, according to claim 15, further comprising adding a second detection reagent to the sample.

29. A method, according to claim 15, wherein the dye has the structure

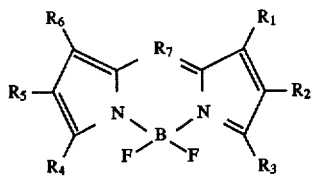

wherein the dye is attached to the polymer at one of $R_1$–$R_7$; and for the remainder of $R_1$–$R_7$ at which the polymer is not attached:

$R_1$, $R_2$, $R_3$, $R_4$, $R_5$ and $R_6$, which may be the same or different, are hydrogen, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or aryl or heteroaryl; or adjacent substituents $R_1$ and $R_2$, and adjacent substituents $R_5$ and $R_6$, when taken in combination form a fused benzo ring that is optionally substituted by hydrogen, halogen, nitro, sulfo, cyano, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons; or substituted or unsubstituted aryl, heteroaryl, aryl-amido, heteroaryl-amido, aryl-oxy, heteroaryl-oxy, aryl-amino, or heteroaryl-amino; or the one or more fused benzo rings are substituted by 1–2 additional fused benzo or heteroaromatic rings;

$R_7$ is nitrogen; or methine; or halogen-, cyano-, alkyl-, perfluoroalkyl-, alkoxy-, alkenyl-, alkynyl-, cycloalkyl-, arylalkyl-, acyl-substituted methine wherein the alkyl portions of each contain fewer than 20 carbons; or aryl- or heteroaryl-substituted methine.

30. A method, according to claim 29, wherein the labeled polymer is a peptide, protein, polysaccharide, oligonucleotide or nucleic acid.

31. A method, according to claim 29, wherein the condition is the presence of an enzyme.

32. A method of detecting a complementary member of a specific binding pair in a sample, comprising:

a) adding to said sample a labeled polymer having conjugated thereto at least 2 molecules of a borapolyaza-s-indacene dye wherein the conjugated dye on the polymer exhibits fluorescence quenching of at least 90% relative to the borapolyaza-s-indacene dye that is unconjugated; wherein the labeled polymer further comprises a covalently bound member of a specific binding pair that is specific for the complementary member;

b) allowing sufficient time for the labeled polymer to form a complex with the complementary member;

c) removing uncomplexed labeled polymer from the sample;

d) exposing the sample to a condition that will degrade the labeled polymer for a time sufficient to degrade the polymer; and e) correlating the appearance of fluorescence in the sample with the presence of the complementary member.

33. A method, as claimed in claim 32, further comprising correlating the location of fluorescence in the sample with the location of the complementary member.

34. A method, according to claim 32, wherein the conjugated dye exhibits fluorescence quenching of at least 98% relative to the unconjugated dye.

35. A method, as claimed in claim 32, wherein the condition is the presence of an enzyme.

36. A method, according to claim 32, wherein the condition is chemical treatment, heat treatment, ionizing radiation, mechanical force, photolysis, sound, ultrasound, drug interaction, changes in ionic strength, applied pressure, or exposure to organic solvents.

37. A method, according to claim 32, wherein the member of a specific binding pair is a protein or an oligonucleotide.

38. A method, according to claim 37, wherein the member of a specific binding pair is an avidin, a streptavidin or an antibody.

39. A method, according to claim 32, wherein the dye has the formula

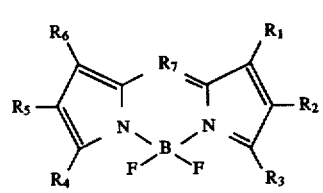

wherein the dye is attached to the polymer at one of $R_1$–$R_7$; and for the remainder of $R_1$–$R_7$ at which the polymer is not attached:

$R_1$, $R_2$, $R_3$, $R_4$, $R_5$ and $R_6$, which may be the same or different, are hydrogen, halogen, nitro, sulfo, cyano, alkyl, perfluoroalkyl, alkoxy, alkenyl, alkynyl, cycloalkyl, arylalkyl, or acyl, wherein the alkyl portions of each contain fewer than 20 carbons; or aryl or heteroaryl; or adjacent substituents $R_1$ and $R_2$, and adjacent substituents $R_5$ and $R_6$, when taken in combination form a fused benzo ring that is optionally substituted by hydrogen, halogen, nitro, sulfo, cyano, alkyl, perfluoroalkyl, alkoxy, alkenyl, alkynyl, cycloalkyl, alkylthio, alkylamido, amino, monoalkylamino or dialkylamino wherein the alkyl portions of each contain fewer than 20 carbons; or substituted or unsubstituted aryl, heteroaryl, aryl-amido, heteroaryl-amido, aryl-oxy, heteroaryl-oxy, aryl-amino, or heteroaryl-amino; or the one or more fused benzo rings are substituted by 1-2 additional fused benzo or heteroaromatic rings;

$R_7$ is nitrogen; or methine; or halogen-, cyano-, alkyl-, perfluoroalkyl-, alkoxy-, alkenyl-, alkynyl-, cycloalkyl-, arylalkyl-, acyl-substituted methine wherein the alkyl portions of each contain fewer than 20 carbons; or aryl- or heteroaryl-substituted methine.

40. A polymer, as claimed in claim 13, that is a casein, collagen, fibronectin or albumin, wherein the dye is attached to the polymer at one of $R_1$–$R_7$, and the rest of $R_1$–$R_7$ are H, methyl, 2-thienyl or 2-pyrrolyl, provided that no more than 4 of the remainder of $R_1$–$R_7$ are non-hydrogen.

* * * * *

UNITED STATES PATENT AND TRADEMARK OFFICE
CERTIFICATE OF CORRECTION

PATENT NO. : 5,719,031
DATED : Feb. 17, 1998
INVENTOR(S) : Haugland et al

It is certified that error appears in the above-identified patent and that said Letters Patent is hereby corrected as shown below:

At col. 2, line 19, "CFTC)" should be --(FTC).
At col. 3, line 61, "mSethine." should be --methine--.
At col. 3, line 63, "mSethine" should be --methine--.
At col. 5, line 59, "CRNase)" should be --(RNase)--.
At col. 8, line 46, "<10,000 daltons" should be --≤10,000 daltons--.
At col. 10, line 16, "photographic fill" should be --photographic film--.
At col. 11, line 39, "fiein;" should be --ficin--.
At col. 14, line 30, "DNA or KNA" should be --DNA or RNA--.
At col. 15, line 2, "503 rim" should be --503 nm--.
At col. 15, line 9, "5 12 nm" should be --512 nm--.
At col. 15, line 38, "100 of either" should be --100 µL of either--.

Signed and Sealed this

Twenty-seventh Day of February, 2001

Attest:

NICHOLAS P. GODICI

Attesting Officer

Acting Director of the United States Patent and Trademark Office